United States Patent [19]

Murai et al.

[11] 4,137,231
[45] Jan. 30, 1979

[54] PROCESS FOR THE ISOLATION OF 2-HYDROXYMETHYL-3,4,5-TRIHYDROXYPIPERIDINE FROM PLANT MATERIAL

[75] Inventors: Hiromu Murai, Otsu; Hiroshi Enomoto; Yoshiaki Yoshikuni, both of Kyoto; Tatsuhiko Kono, Kyoto; Masahiro Yagi, Otsu, all of Japan

[73] Assignee: Nippon Shinyaku Co., Ltd., Kyoto, Japan

[21] Appl. No.: 752,149

[22] Filed: Dec. 20, 1976

[30] Foreign Application Priority Data

Dec. 29, 1975 [JP] Japan .............................. 50/157423

[51] Int. Cl.$^2$ ........................................... C07D 211/46
[52] U.S. Cl. .................................................. 546/242
[58] Field of Search ...................................... 260/293.9

[56] References Cited

PUBLICATIONS

*Chemical Abstracts,* 47,7038b, (1953), [Oku, M., *J. Sericult. Sci.,* Japan 19, 309–311, (1950)].
*Chemical Abstracts,* 25, 1286'(1931), [Min, P., *Folia Pharmacol Japan,* 11(#2), 181–187, Breviaria 13, (1930)].

*Primary Examiner*—Henry R. Jiles
*Assistant Examiner*—Richard A. Schwartz
*Attorney, Agent, or Firm*—Jacobs & Jacobs

[57] ABSTRACT

2-Hydroxymethyl-3,4,5-trihydroxypiperidine is obtained from the mulberry plant through extraction, optionally with further purification through ion exchange or chromatographic treatment.

5 Claims, No Drawings

PROCESS FOR THE ISOLATION OF 2-HYDROXYMETHYL-3,4,5-TRIHYDROXYPIPERIDINE FROM PLANT MATERIAL

DETAILED DESCRIPTION

The present invention relates to a new method for obtaining 2-hydroxymethyl-3,4,5-trihydroxypiperidine, a known compound whose chemical synthesis has been described for example in Tetrahedron, 24 2125 (1968); J. Antibiotics, Ser. A, 19(6), 288 (1966); and Chem. Pharm. Bull. (Tokyo), 16(5), 962 (1968). As is described in greater detail in the copending application of Ohata et al., Ser. No. 752,006 filed Dec. 20, 1976, now U.S. Pat. 4,065,562, the compound also exhibits a strong antidiabetic action as well as inhibitory activity on lipid biosynthesis.

According to the present invention, it has now been discovered that 2(R),3(R),4(R),5(S)-2-hydroxymethyl-3,4,5-trihydroxypiperidine, which can be represented by the formula

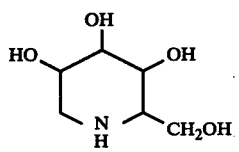

can be obtained from the mulberry plant of the genus Morus through extracton with water or a polar organic solvent, the compound being isolated from the extract. If desired, the compound can be further purified by subjecting it to treatment with an ion exchange resin or by chromatographic methods utilizing activated carbon-celite, or silica gel columns.

Although diuretic and antitussive properties have been ascribed to the Mori Cortex in Chinese medicine, the compound prepared according to the present process is not the active diuretic or antitussive component of that material. Moreover, although the compound has been prepared chemically, as noted above, it has not previously been isolated from naturally occurring substances.

Extraction of the compound from mulberry according to this invention is as follows. The fine and dry powder of a plant of Morus genus, such as for example, *Morus alba* L., *M. bombycis* Koidz or *M. Lhou* Koidz (*M. multicaulis* Perr.), preferably dry powder of roots and barks of such plant, is extracted with water or a polar organic solvent such as methanol. The resulting extract is concentrated and treated with an organic solvent of less polarity or no polarity such as ethyl acetate, ether, n-hexane or such. The soluble matter is removed and the remaining water-soluble substance is subjected to a column chromatography with an ion exchange resin to isolate the active principal therefrom. It is also advisable to use active carbon-celite as filler of the column. The thus isolated crystals, as determined from the mass spectral data, showed molecular weigh of 163 and the following physical properties:

Elemental analysis — Found: C, 44.13%; H, 8.41%, N, 8.67%. Calcd. for $C_{16}H_{13}NO_4$: C, 44.16%; H, 8.03%; N, 8.58%.

Melting point: 204°–205° C

Optical rotation: $[\alpha]^{22}D + 45.1°$ (C, 0.96 $H_2O$)

Further chemical examination revealed that this material can be expressed by the above formula.

The extraction of the compound (I) according to this invention will be illustrated in some detail in the following Examples:

EXAMPLE 1

One kilogram of commercially available dry Mori Cortex was powdered by a crusher and then extracted by maceration three times for 24 hours with 2 liters of methanol. The obtained extract solutions were combined and concentrated in vacuo to give 80 grams of methanol extract. This methanol extract was dissolved and suspended in ten times as much amount of water and washed with ethyl acetate. After removing the ethyl acetate soluble components, the water-soluble matter was subjected to chromatography with an Amberlite CG-400 (OH type) 1-kg column. The water eluate was collected and further subjected to chromatography with Dowex 50W × 4 (H type) 1-lit. column. The column developed with water to eliminate the neutral substances and other impurities. The material was eluted with 0.3 N ammonia water, collecting 1 liter of elutate after the pH of the eluate has shifted from neutral to alkali range. Water was removed by distillation in vacuo from the eluted product to give a brown solid mass, which was crystallized from methanol to give 570 mg of colorless crystals. The yield was 0.057% as calculated on the basis of the amount of dry starting material.

EXAMPLE 2

The methanol extraction residue of the commercial Mori Cortex used in Example 1 was extracted by maceration two times for 24 hours with 5 liters of water. The obtained extract solution was concentrated under vacuum to approximately 1 liter and subjected to chromatography on a Dowex 1 × 2 1-lit. column. The water eluted portion was further subjected to chromatography on a 1-lit. Dowex 50W × 4 column. The column was developed with water and, after removing the neutral matter and other impurities, eluted with 0.3 N ammonia water.

Water was removed by distillation in vacuo from the eluted solution to give a brown solid mass, which was then dissolved in methanol, subjected to a treatment with a small amount of active carbon and crystallized, yielding 850 mg of colorless crystals. The yield was 0.085% was calculated on the basis of the amount of dry starting material. From the processes of Examples 1 and 2 combined together, 1420 mg of the desired material could be obtained from 1 kg of commercial dry Mori Cortex at the yield of 0.142%.

EXAMPLE 3

Five hundred grams of dry barks and roots of *M. Lhou* Koidz (*M. multicaulis* Perr.) was powdered and extracted by maceration two times for 24 hours with 3 liters of water. The extracts were concentrated under vacuum to about 1 liter, subjected to a column chromatograph with 1 kg of a mixture of equal amounts of active carbon and celite, and then developed with water to remove the inorganic salts and other impurities. The product was further developed with 2 liters of a mixture of equal amounts of ethanol and water and the ethanol and water eluted matter was concentrated in vacuo and evaporated to dryness to give a brown solid mass. This brown solid mass was further extracted with hot methanol and the methanol soluble portion was treated with active carbon and then concentrated to give 820 mg of colorless crystals. The yield was 0.164% as calculated on the basis of the amount of dry starting material.

EXAMPLE 4

Barks of *M. alba* L. and leaves of *M. bombycis* Koidz were treated after the manner of Examples 1 and 2 to obtain the similar medicinal materials at the yields of 0.052% and 0.015%, respectively.

What is claimed is:

1. The process which comprises extracting 2-hydroxymethyl-3,4,5-trihydroxypiperidine from plant material of the Morus genus with water or a polar organic solvent and isolating the 2-hydroxymethyl-3,4,5-trihydroxypiperidine from the resultant extract.

2. The process according to claim 1 wherein said extract is chromatographed on an activated carbon-celite silica gel.

3. The process according to claim 1 wherein said extract is treated with an ion exchange resin.

4. The process according to claim 1 wherein said plant material is extracted with at least one member selected from the group of water and methanol.

5. The process according to claim 4 wherein said extracts are washed with an organic solvent of less polarity than methanol to remove any components soluble in ethyl acetate.

* * * * *